United States Patent
Gat et al.

(10) Patent No.: US 8,406,490 B2
(45) Date of Patent: Mar. 26, 2013

(54) SYSTEM AND METHODS FOR DETERMINATION OF PROCEDURE TERMINATION

(75) Inventors: Daniel Gat, Haifa (IL); Ofra Zinaty, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 1174 days.

(21) Appl. No.: 12/059,420

(22) Filed: Apr. 30, 2008

(65) Prior Publication Data

US 2009/0274347 A1  Nov. 5, 2009

(51) Int. Cl.
*G06K 9/20* (2006.01)
*G06K 9/36* (2006.01)
*A61B 1/00* (2006.01)

(52) U.S. Cl. .................... 382/128; 382/130; 600/118

(58) Field of Classification Search .......... 382/128–133; 600/118, 407–464
See application file for complete search history.

(56) References Cited

U.S. PATENT DOCUMENTS

| | | | |
|---|---|---|---|
| 3,662,267 A | 5/1972 | Reed | |
| 4,219,821 A | 8/1980 | Selim | |
| 4,278,077 A | 7/1981 | Mizumoto | |
| 4,329,881 A | 5/1982 | Schloss | |
| 4,896,967 A | 1/1990 | Douglas-Hamilton et al. | |
| 5,042,486 A | 8/1991 | Pfeiler et al. | |
| 5,211,165 A | 5/1993 | Dumoulin et al. | |
| 5,279,607 A | 1/1994 | Schentag et al. | |
| 5,429,132 A | 7/1995 | Guy et al. | |
| 5,515,853 A | 5/1996 | Smith et al. | |
| 5,592,180 A | 1/1997 | Yokev et al. | |
| 5,604,531 A | 2/1997 | Iddan et al. | |
| 5,697,377 A | 12/1997 | Wittkampf | |
| 5,736,958 A | 4/1998 | Turpin | |
| 5,802,135 A | 9/1998 | Wahlrab | |
| 5,913,820 A | 6/1999 | Bladen et al. | |
| 5,993,378 A | 11/1999 | Lemelson | |
| 6,172,640 B1 | 1/2001 | Durst et al. | |
| 6,188,355 B1 | 2/2001 | Gilboa | |
| 6,190,395 B1 | 2/2001 | Williams | |
| 6,233,476 B1 | 5/2001 | Strommer et al. | |
| 6,240,312 B1 | 5/2001 | Alfano et al. | |
| 6,453,190 B1 | 9/2002 | Acker et al. | |
| 6,580,938 B1 | 6/2003 | Acker | |
| 6,690,963 B2 | 2/2004 | Ben-Haim et al. | |
| 6,904,308 B2 | 6/2005 | Frisch et al. | |

(Continued)

FOREIGN PATENT DOCUMENTS

| | | |
|---|---|---|
| DE | 344 0177 | 5/1986 |
| EP | 0 667 115 | 8/1995 |

(Continued)

OTHER PUBLICATIONS

European Search Report for European Application No. 08 154 317 dated Aug. 4, 2008.

(Continued)

*Primary Examiner* — Melissa Koval
*Assistant Examiner* — Emily Chan
(74) *Attorney, Agent, or Firm* — Pearl Cohen Zedek Latzer, LLP

(57) ABSTRACT

This invention relates to a system and methods for determining the initiation and/or the termination of an autonomous in vivo imaging procedure, such as by a capsule imaging the gastro intestinal tract.

15 Claims, 4 Drawing Sheets

U.S. PATENT DOCUMENTS

| | | | |
|---|---|---|---|
| 6,934,573 B1 | 8/2005 | Glukhovsky et al. | |
| 6,950,690 B1 | 9/2005 | Meron et al. | |
| 7,009,634 B2 | 3/2006 | Iddan et al. | |
| 7,104,952 B2 * | 9/2006 | Iddan et al. | 600/118 |
| 7,144,366 B2 | 12/2006 | Takizawa et al. | |
| 7,319,781 B2 | 1/2008 | Chen et al. | |
| 7,354,397 B2 | 4/2008 | Fujita et al. | |
| 7,585,283 B2 * | 9/2009 | Kraizer et al. | 600/593 |
| 7,922,653 B2 * | 4/2011 | Homan | 600/118 |
| 2002/0103417 A1 | 8/2002 | Gazdzinski | |
| 2002/0198470 A1 | 12/2002 | Imran et al. | |
| 2003/0013370 A1 | 1/2003 | Glukhovsky | |
| 2003/0167000 A1 | 9/2003 | Mullick et al. | |
| 2003/0213495 A1 | 11/2003 | Fujita et al. | |
| 2003/0214580 A1 | 11/2003 | Iddan | |
| 2004/0087832 A1 * | 5/2004 | Glukhovsky et al. | 600/118 |
| 2004/0176685 A1 | 9/2004 | Takizawa et al. | |
| 2005/0261551 A1 | 11/2005 | Couvillon, Jr. | |
| 2006/0120484 A1 | 6/2006 | Matsumoto et al. | |
| 2006/0146739 A1 | 7/2006 | Matsumoto et al. | |
| 2006/0149126 A1 | 7/2006 | Ertas et al. | |
| 2006/0183993 A1 | 8/2006 | Horn | |
| 2007/0225560 A1 | 9/2007 | Avni et al. | |
| 2008/0033257 A1 | 2/2008 | Yokoi et al. | |
| 2008/0039687 A1 | 2/2008 | Shimizu et al. | |
| 2008/0177136 A1 | 7/2008 | Wang | |
| 2008/0255635 A1 * | 10/2008 | Bettesh et al. | 607/60 |
| 2009/0005642 A1 * | 1/2009 | Shigemori et al. | 600/118 |

FOREIGN PATENT DOCUMENTS

| | | |
|---|---|---|
| EP | 1867280 | 12/2007 |
| EP | 1 872 710 | 1/2008 |
| JP | 57-45833 | 5/1982 |
| JP | 02-31738 | 2/1990 |
| JP | 4-109927 | 4/1992 |
| JP | 1992-144533 | 5/1992 |
| JP | 6154191 | 6/1994 |
| JP | 6285044 | 10/1994 |
| JP | 1995/111985 | 5/1995 |
| JP | 7111985 | 5/1995 |
| JP | 7255692 | 10/1995 |
| JP | 2001046358 | 2/2001 |
| JP | 2001231186 | 8/2001 |
| JP | 2001231187 | 8/2001 |
| WO | WO 98/11816 | 3/1998 |
| WO | WO9837926 | 9/1998 |
| WO | WO 99/32028 | 7/1999 |
| WO | WO 00/10456 | 3/2000 |
| WO | WO 01/06917 | 2/2001 |
| WO | WO 01/08548 | 2/2001 |
| WO | WO 03/021529 | 3/2003 |
| WO | WO 03/028224 | 4/2003 |
| WO | WO 03/090618 | 11/2003 |
| WO | WO03096889 | 11/2003 |
| WO | WO 2004/036803 | 4/2004 |
| WO | WO 2006/059331 | 6/2006 |
| WO | WO 2006/077529 | 7/2006 |
| WO | WO 2007/026891 | 3/2007 |
| WO | WO 2007/066288 | 6/2007 |

OTHER PUBLICATIONS

European Office Action for European Application No. 08 154 317 dated Mar. 31, 2006.

Park, et al., "*A Technique for Position Detection of Miniatured Wireless Telemetry Module in the Human Body*", Proceedings of the 32$^{nd}$ ISR (International Symposium on Robotics), Apr. 19-21, 2001, pp. 1888-1892.

Park, et al., "*Design of Bi-directional and Multi-Channel Miniaturized Telemetry Module for Wireless Endoscopy*", 2$^{nd}$ Annual International IEEE-EMBS Special Topic Conference on Microtechnologies in Medicine & Biology, May 2-4, 2002, Madison, Wisconsin USA pp. 273-276.

Park, et al., "*Design of Miniaturized Telemetry Module for Bi-Directional Wireless Endoscopy*", May 2-4, 2002.

Park, et al., "*A Technique for Localization of Biomedical Telemetry Sensor in Human Body*", Proceedings of the International Sensor Conference 2001, Seoul, Korea.

Nam, et al., "*A method for Position Detection of the wireless capsule endoscopes Module Using the Solution of Nonlinear Simultaneous Equations*", Sensors Conference 2002, p. 377.

Nam, et al., "*A method for Position Detection of Miniaturized Telemetry Module Using the Solution of Nonlinear Simultaneous Equations*", 2002.

"Localization of a wireless capsule endoscope in the GI Tract", Gastrointestinal Endoscopy 2001;53:AB126.

www.ibcdigital.com/ibc/animation_galleries/visualization.

Office Action for U.S. Appl. No. 10/150,018 mailed on May 18, 2004.
Office Action for U.S. Appl. No. 11/073,633 mailed on Jun. 9, 2008.
Office Action for U.S. Appl. No. 11/073,633 mailed on Feb. 18, 2009.
Office Action for U.S. Appl. No. 11/319,660 mailed on Apr. 29, 2009.
Partial European Search Report for European Appl. No. 09 00 4718 dated Jun. 16, 2009.
Office Action for European Patent Application No. 09004718.4 mailed Jun. 18, 2012.

* cited by examiner

SYSTEM AND METHODS FOR DETERMINATION OF PROCEDURE TERMINATION

FIELD OF INVENTION

The present invention relates to an in-vivo device and method such as for imaging an in-vivo lumen. More specifically, the present invention relates to a method and apparatus in an in-vivo system for determining the termination of an in-vivo procedure performed with an autonomous in-vivo imaging device.

BACKGROUND OF THE INVENTION

Known devices may be helpful in providing in-vivo sensing, such as imaging or pH sensing. Autonomous in-vivo sensing devices, such as swallowable or ingestible capsules or other devices, may move through a body lumen, sensing as they move along. An autonomous in-vivo sensing device such as an imaging device may include, for example, an imager for obtaining images from inside a body cavity or lumen, such as the gastrointestinal (GI) tract while the in-vivo imaging device passes through the GI lumen. The imager may, for example, be associated with an optical system, and optionally a transceiver and an antenna. Some of these devices use a wireless connection to transmit image data. Other devices, systems and methods for in-vivo sensing of passages or cavities within a body, and for sensing and gathering information (e.g., image information, pH information, temperature information, electrical impedance information, pressure information, etc.), are known in the art.

Known methods exist for determining whether a capsule has been evacuated from the body. According to these methods, information of the living body is sensed by an in vivo imaging capsule, and the information is sent to an external receiver. The information may include image information, pH information, pressure information, electrical impedance, amounts/concentration of specific chemical materials or temperature information. Based on the sensed information, it is determined whether the capsule has been evacuated from the body. Based on the determination, a notification is provided, notifying that the capsule has been evacuated from the body.

SUMMARY OF THE INVENTION

The present invention relates in one embodiment to a method for determining termination of an in-vivo imaging procedure and introduces a system that provides notification regarding the end of the procedure.

According to one embodiment, there is provided a method of determining termination of an in vivo image capturing procedure by an autonomous device comprising determining if the autonomous device is transmitting a signal. According to one embodiment, if the device is transmitting a signal, the signal type of said signal may be detected. The signal strength may also be measured. Based on the detected signal type, it may be determined whether the autonomous device has completed the image capturing procedure. In some embodiments, if it is determined that the autonomous device has completed the image capturing procedure, a notification is provided for example to the patient or to the health care professional, regarding the termination of the procedure.

In some embodiments, the method may include determining whether the autonomous device is in vivo, based on the signal that is transmitted from the capsule and detected by an external receiver, and providing a notification of whether the autonomous device is in vivo or has exited the body.

In some embodiments, the method may include analyzing the captured in vivo images and determining whether the autonomous device is in vivo based on the image analysis.

According to one embodiment, there is provided a method of determining termination of an in vivo image capturing procedure by an autonomous device. The method may include the step of determining if the autonomous device is transmitting signals. If the device is not transmitting signals, termination of the image capturing procedure may be determined.

According to another embodiment, there is provided a system for determining termination of an in vivo image capturing procedure comprising an autonomous imaging device comprising a transceiver to transmit signals wirelessly, a receiving unit to receive signals from the imaging device and to determine the signal type, a measuring device to measure strength of the received signals, and a determining means which may determine whether the image capturing procedure has terminated. In some embodiments, the determination is based on analysis of the type and/or strength of the received signals. The determining means may be included in the receiving unit, in the autonomous imaging device or in a workstation, for example a workstation which receives the images from the receiving unit and displays them to a user.

In a preferred embodiment, if the imaging device's power supply is low, for example the battery has a low voltage indication, the device may quit the image capturing mode and switch to a beacon mode. When the device stops transmission in an image capturing mode, it may be determined that the procedure has terminated and that the device is in vivo. If the signal transmission stops and there is no previous indication of low voltage, it may be determined that the procedure has terminated and that the device has exited the patient's body.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein.

Figure 1:
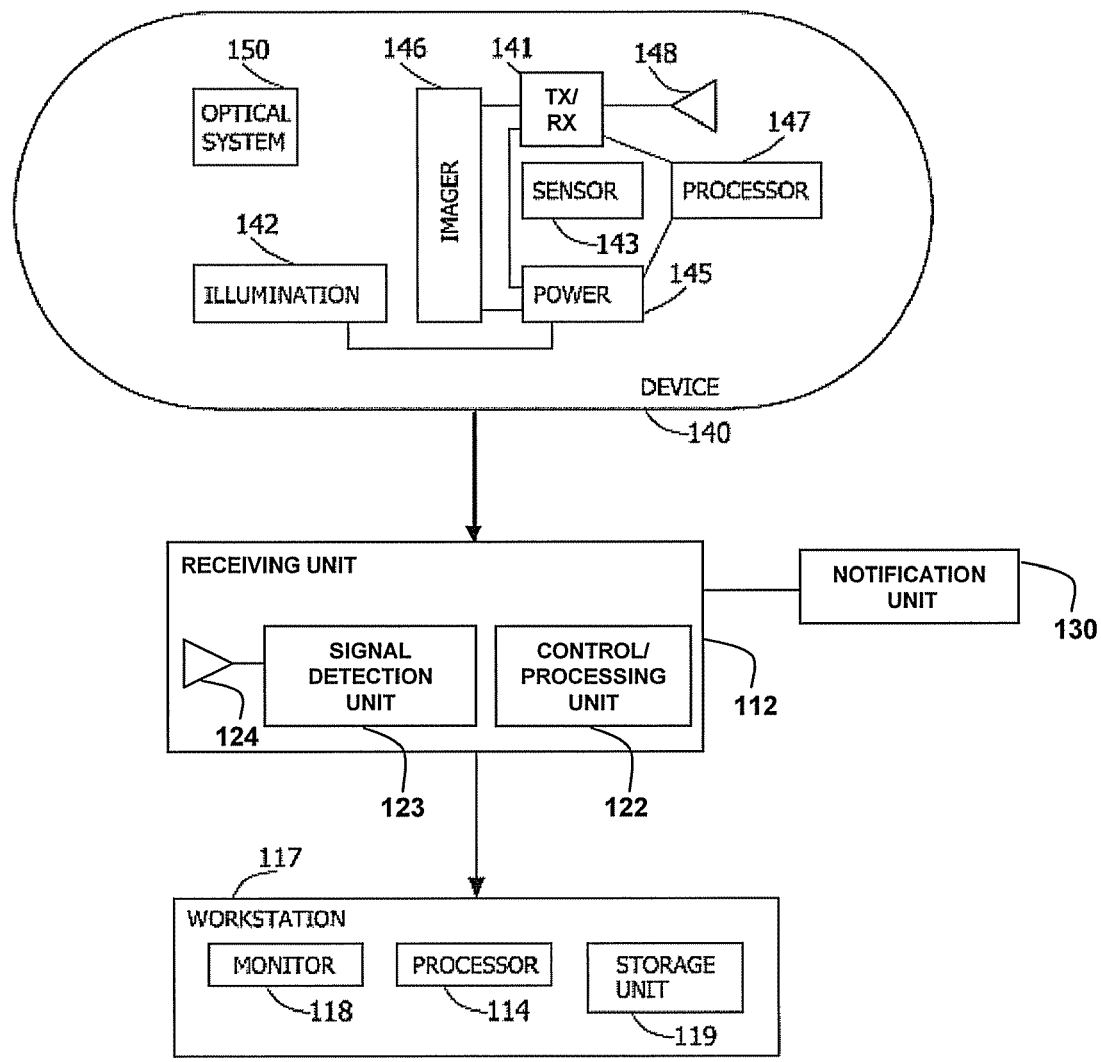
FIG. 1 is a schematic illustration of an in-vivo system according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Some embodiments of the present invention are directed to an in-vivo device that may be inserted into a body lumen, e.g., the gastro-intestinal (GI) tract, for example, from outside the body. Some embodiments are directed to a typically one time use or partially single use detection and/or analysis device. Some embodiments are directed to a typically swallowable in-vivo device that may passively or actively progress through a body lumen, e.g., the gastro-intestinal (GI) tract, for example, pushed along by natural peristalsis. Some embodiments are directed to in-vivo sensing devices that may be passed through other body lumens, for example, through blood vessels, the reproductive tract, or the like. The in-vivo device may be, for example, a sensing device, an imaging device, a diagnostic device, a detection device, an analysis device, a therapeutic device, or a combination thereof. In some embodiments, the in-vivo device may include an image sensor or an imager and/or other suitable components. Some embodiments of the present invention may be directed to other imaging devices, not necessarily in-vivo imaging.

Devices, systems and methods according to some embodiments of the present invention, including for example in-vivo sensing devices, receiving systems and/or display systems, may be similar to embodiments described in U.S. Pat. No. 5,604,531 to Iddan et al., entitled "In-vivo Video Camera System", and/or in U.S. Pat. No. 7,009,634 to Iddan et al., entitled "Device for In-Vivo Imaging", all of which are hereby incorporated by reference in their entirety. Devices, systems and methods according to some embodiments of the present invention, may be similar to embodiments described in PCT Patent Application Publication Number WO2006059331, entitled "TWO-WAY COMMUNICATION IN AN AUTONOMOUS IN VIVO DEVICE", which discloses an autonomous in-vivo sensing device that includes an in-vivo transceiver to both transmit wireless signals to for example an external receiver, and to receive wireless signals from for example an external transmitter. The application further discloses that wireless signals received by the in-vivo transceiver may be or may include command or control signals that may activate, de-activate or alter an operational state of one or more functions of the in-vivo device. The wireless signals transmitted by the in-vivo transceiver may be or include sensory data such as for example image data that may be collected by the in-vivo sensing device.

Devices and systems as described herein may have other configurations and/or sets of components. For example, an external receiver/recorder unit, a processor and a monitor, e.g., in a workstation, such as those described in the above publications, may be suitable for use with some embodiments of the present invention. Devices and systems as described herein may have other configurations and/or other sets of components. For example, the present invention may be practiced using an endoscope, needle, stent, catheter, etc. Some in-vivo devices may be capsule shaped, or may have other shapes, for example, a peanut shape or tubular, spherical, conical, or other suitable shapes.

Some embodiments of the present invention may include, for example, a typically swallowable in-vivo device. In other embodiments, an in-vivo device need not be swallowable and/or autonomous, and may have other shapes or configurations. Some embodiments may be used in various body lumens, for example, the GI tract, blood vessels, the urinary tract, the reproductive tract, or the like.

Embodiments of the in-vivo device are typically autonomous and are typically self-contained. For example, the in-vivo device may be or may include a capsule or other unit where all the components are substantially contained within a container, housing or shell, and where the in-vivo device does not require any wires or cables to, for example, receive power or transmit information. The in-vivo device may communicate with an external receiving and display system to provide display of data, control, or other functions. For example, power may be provided by an internal battery or an internal power source, or using a wired or wireless power-receiving system. Other embodiments may have other configurations and capabilities. For example, components may be distributed over multiple sites or units; and control information or other information may be received from an external source.

Devices, systems and methods in accordance with some embodiments of the invention may be used, for example, in conjunction with a device which may be inserted into a human body or swallowed by a person. However, embodiments of the invention are not limited in this regard, and may be used, for example, in conjunction with a device which may be inserted into, or swallowed by, a non-human body or an animal body. Other embodiments of the invention need not be used with in vivo imaging devices, and may be used for enhancing images obtained by other types of imaging devices, such as digital cameras, or virtual imaging devices.

FIG. 1 schematically illustrates an in-vivo system in accordance with some embodiments of the present invention. One or more components of the system may be used in conjunction with, or may be operatively associated with, the devices and/or components described herein or other in-vivo devices in accordance with embodiments of the invention.

In some embodiments, the system may include a device 140 having a sensor, e.g., an imager 146, one or more illumination sources 142, a power source 145, and a transceiver 141. In some embodiments, device 140 may be implemented using a swallowable capsule, but other sorts of devices or suitable implementations may be used. Outside a patient's body may be, for example, an external receiver/recorder 112. A storage unit 119 which may be or include for example one or more of a memory, a database, etc. or other storage systems, a processor 114, and a monitor 118. In some embodiments, for example, processor 114, storage unit 119 and/or monitor 118 may be implemented as a workstation 117, e.g., a computer or a computing platform.

Transceiver 141 may operate using radio waves; but in some embodiments, such as those where device 140 is or is included within an endoscope, transceiver 141 may transmit/receive data via, for example, wire, optical fiber and/or other suitable methods. Other known wireless methods of transmission may be used. Transceiver 141 may include, for example, a transmitter module or sub-unit and a receiver module or sub-unit, or an integrated transceiver or transmitter-receiver. In one embodiment, transceiver 141 includes at least a modulator for receiving an image signal from the sensor 146, a radio frequency (RF) amplifier, an impedance matcher and an antenna 148. The modulator converts the input image signal having a cutoff frequency $f_c$ of less than 5 MHz to an RF signal having a carrier frequency $f_c$, typically in the range of 1 GHz. While in one embodiment, the signal is an analog signal, the modulating signal may be digital rather than analog. The carrier frequency may be in other bands, e.g., a 400 MHz band. The modulated RF signal has a bandwidth of ft. The impedance matcher matches the impedance of the circuit to that of the antenna. Other transceivers or arrangements of transceiver components may be used. For example, alternate embodiments may not include a matched antenna or may include a transceiver without a matching circuit. In alternate embodiments, the device 140 may have different configurations and include other sets of components. Other frequencies may be used. In yet further embodiments, sensors other than image sensors may be used, such as pH meters, temperature sensors, pressure sensors, etc. and input RF signals other than image signals may be used.

The transceiver 141 may send different types of signals, including for example telemetry signals, image signals and beacon signals. Other types of signals may be transmitted by transceiver 141. The signal types may vary in several parameters, such as the length of the signal burst, the transmission frequency of the signal, the rate of sending the signal, the power used to transmit the signal, the content of the sent signal, etc. Information sent from the device 140 may include information sensed by sensors in the device such as images, pH, temperature, location and pressure. Information sent from the device 140 may include telemetry information, regarding the capsule ID, time counter, image type data and the status of components in the device, such as current image capturing mode of the imager or estimated remaining power of the device power source. The signals may be sent separately or as part as a larger frame, for example a frame including both telemetry-type and image-type signals. Beacon signals may typically be transmitted separately, and not in a frame which may include image data or other types of signals.

Device 140 typically may be or may include an autonomous swallowable capsule, but device 140 may have other shapes and need not be swallowable or autonomous. Embodiments of device 140 are typically autonomous, and are typically self-contained. For example, device 140 may be a capsule or other unit where all the components are substantially contained within a container or shell, and where device 140 does not require any wires or cables to, for example, receive power or transmit information. In some embodiments, device 140 may be autonomous and non-remote-controllable; in another embodiment, device 140 may be partially or entirely remote-controllable.

In some embodiments, device 140 may include an in-vivo video camera, for example, imager 146, which may capture and transmit images of, for example, the GI tract while device 140 passes through the GI lumen. Other lumens and/or body cavities may be imaged and/or sensed by device 140. In some embodiments, imager 146 may include, for example, a Charge Coupled Device (CCD) camera or imager, a Complementary Metal Oxide Semiconductor (CMOS) camera or imager, a digital camera, a stills camera, a video camera, or other suitable imagers, cameras, or image acquisition components.

In some embodiments, imager 146 in device 140 may be operationally connected to transceiver 141. Transceiver 141 may transmit images to, for example, external transceiver or receiver/recorder 112 (e.g., through one or more antennas), which may send the data to processor 114 and/or to storage unit 119. Transceiver 141 may also include control capability, although control capability may be included in a separate component, e.g., processor 147. Transceiver 141 may include any suitable transmitter able to transmit image data, other sensed data, and/or other data (e.g., control data, beacon signal, etc.) to a receiving device. Transceiver 141 may also be capable of receiving signals/commands, for example from an external transceiver. For example, in some embodiments, transceiver 141 may include an ultra low power Radio Frequency (RF) high bandwidth transmitter, possibly provided in Chip Scale Package (CSP).

In some embodiments, transceiver 141 may transmit/receive via antenna 148. Transceiver 141 and/or another unit in device 140, e.g., a controller or processor 147, may include control capability, for example, one or more control modules, processing module, circuitry and/or functionality for controlling device 140, for controlling the operational mode or settings of device 140, and/or for performing control operations or processing operations within device 140. According to some embodiments, transceiver 141 may include a receiver which may receive signals (e.g., from outside the patient's body), for example, through antenna 148 or through a different antenna or receiving element. According to some embodiments, signals or data may be received by a separate receiving device in device 140.

Power source 145 may include one or more batteries or power cells. For example, power source 145 may include silver oxide batteries, lithium batteries, other suitable electrochemical cells having a high energy density, or the like. Other suitable power sources may be used. For example, power source 145 may receive power or energy from an external power source (e.g., an electromagnetic field generator), which may be used to transmit power or energy to in-vivo device 140.

In some embodiments, power source 145 may be internal to device 140, and/or may not require coupling to an external power source, e.g., to receive power. Power source 145 may provide power to one or more components of device 140 continuously, substantially continuously, or in a non-discrete manner or timing, or in a periodic manner, an intermittent manner, or an otherwise non-continuous manner. In some embodiments, power source 145 may provide power to one or more components of device 140, for example, not necessarily upon-demand, or not necessarily upon a triggering event or an external activation or external excitement. In a preferred embodiment, power source 145 may be operationally coupled to a data bus, and may provide data regarding the status of different battery parameters, for example upon request. The battery data parameters that may be read from the battery include the estimated time left to operate in a specific mode, current capacity, voltage, battery and/or manufacturer identification codes, maximum error percentage of the capacity, etc. In one embodiment, during every transmission of a signal, the voltage of power source 145 is measured. If the voltage falls below a programmable threshold, for example when the voltage falls below 20% of its initial or maximal value, or below an absolute value such as 2.4V, the device may quit the image capturing mode, and transit to another mode, depending on preprogrammed commands or commands received from an external control unit in real time. In the same manner, if the voltage falls below a programmable threshold, the device may stop (or start) a beacon signal transmission mode, which will be explained in detail hereinbelow.

Optionally, in some embodiments, transceiver 141 may include a processing unit, processor or controller, for example, to process signals and/or data generated by imager 146. In another embodiment, the processing unit may be implemented using a separate component within device 140, e.g., controller or processor 147, or may be implemented as an integral part of imager 146, transceiver 141, or another component, or may not be needed. The processing unit may include, for example, a Central Processing Unit (CPU), a Digital Signal Processor (DSP), a microprocessor, a controller, a chip, a microchip, a controller, circuitry, an Integrated Circuit (IC), an Application-Specific Integrated Circuit (ASIC), or any other suitable multi-purpose or specific processor, controller, circuitry or circuit. In some embodiments, for example, the processing unit or controller may be embedded in or integrated with transceiver 141, and may be implemented, for example, using an ASIC.

In some embodiments, imager 146 may acquire in-vivo images continuously, substantially continuously, or in a non-discrete manner, for example, not necessarily upon-demand, or not necessarily upon a triggering event or an external activation or external excitation, or in a periodic manner, an intermittent manner, or an otherwise non-continuous manner.

An imaging or image capturing procedure may include the time period during which the imager 146 is capturing images and the transceiver 141 is transmitting the image data to the receiving unit 112. The imaging procedure may be terminated or completed, for example due to a time-out indication, or due to low voltage in the power source 145, or due to an external control command. Such commands may be received by the device 140 from an external control unit which may be a separate unit located outside of the patient's body or may be integrated, for example with the receiving unit 112. The external control unit may be, for example, the control/processing unit 122 integrated within receiving unit 112. In one embodiment, the device power source 145 may transmit an indication through transceiver 141, notifying the control/processing unit 122 of a low battery status. The imaging device processor 147, or another unit operatively connected to the battery, may sample internal registers in the battery to determine, for example, the current battery status, or other battery parameters. Control/processing unit 122 may, in response, transmit a control command to device 140 to temporarily or permanently stop the imaging procedure. The transmission power may be controlled in real time or preprogrammed, for example per signal type. The beacon signal is typically transmitted by the transceiver 141, but may be transmitted by another unit, for example an RF transmission unit. The beacon signal may be transmitted with relatively low power, so as to conserve device 140 battery power. In a preferred embodiment, the beacon signal does not contain any in-vivo information that is sensed by a sensor in the capsule. For example, the beacon signal will not contain any in-vivo image information, temperature or pressure information. The purpose of the beacon may be to announce the capsule's presence/location, and/or to enable determining that the battery is not completely depleted and that the capsule is still transmitting.

In comparison to beacon signals, image signals sent by the device may be transmitted with higher power in order to verify optimal reception by the receiving unit 112.

In some embodiments, transceiver 141 may transmit image data continuously, or substantially continuously, for example, not necessarily upon-demand, or not necessarily upon a triggering event or an external activation or external excitement; or in a periodic manner, an intermittent manner, or an otherwise non-continuous manner. Transceiver 141 may transmit other data, such as telemetry data or beacon signals. The beacon signals may be bursts transmitted in fixed time periods, for example a burst once every second or once every 10 seconds. Other configurations of time periods may be used, and the configuration may be changed depending on, for example, time parameters, power parameters or received image parameters. The beacon signal may be transmitted in variable time periods or rates, and the device 140 may be configured on-the-fly to change the beacon transmission period, rate or regularity. Typically, the beacon signal bursts contain only internal data from the device 140, for example telemetry data or current state of internal components such as the battery status, so no video or image data is transmitted during these bursts. Typically the length of the burst may be between 10 to 100 milliseconds. According to some embodiments, the beacon signal frequency may be lower than the frequency used for image data, for example, in order to conserve power. Device 140 may be preprogrammed or may receive a command to transmit the beacon signal for example once every 10 seconds for 60 minutes, once every 20 seconds for the next 24 hours, and once every 60 seconds for the rest of the battery's life. If another power source is used in device 140, the beacon may continue as long as there's enough power to transmit the signal. A control command may be received, for example, from the external control/processing unit 122.

According to some embodiments, the beacon signal may be transmitted after the device's image capturing procedure is completed, stopped, or terminated. The image capturing procedure may be stopped either permanently or temporarily, for example when the image capturing procedure is stopped temporarily, the device may start transmitting a certain type of beacon signal, or the beacon signal may be transmitted at a specific power intensity, and when the image capturing procedure is resumed, the transmission of the beacon signal may be stopped. If the image capturing procedure is stopped permanently, the device may transmit another type of beacon signal. Such signals may indicate that the imaging procedure is terminated. The beacon signal transmission strength or frequency may also be changed, for example to a predetermined value which may be lower than the image signal transmission strength/frequency, such that the received signal strength/frequency at the receiving unit may indicate whether the device has completed the image capturing procedure. The beacon signal may be produced with a small frame size, for example a frame of 10 lines, 250 bytes each. Other frame sizes may be used. The transmission time may be very short, for example if the transmission rate is 8 [Mbit/s], the beacon signal transmission length value may be 2.8 [mSec]. Comparably, a typical image data frame may be transmitted in, for example, 18 [mSec]. Typically, the beacon signal will be transmitted in a very low frame rate.

In some embodiments, device 140 may include one or more illumination sources 142, for example one or more Light Emitting Diodes (LEDs), "white LEDs", or other suitable light sources. Illumination sources 142 may, for example, illuminate a body lumen or cavity being imaged and/or sensed. An optical system 150, including, for example, one or more optical elements, such as one or more lenses or composite lens assemblies, one or more suitable optical filters, or any other suitable optical elements, may optionally be included in device 140 and may aid in focusing reflected light onto imager 146, focusing illuminating light, and/or performing other light processing operations.

In some embodiments, the components of device 140 may be enclosed within a housing or shell, e.g., capsule-shaped, oval, or having other suitable shapes. The housing or shell may be substantially transparent, and/or may include one or more portions, windows or domes that may be substantially transparent. For example, one or more illumination source(s) 142 within device 140 may illuminate a body lumen through a transparent, window or dome; and light reflected from the body lumen may enter the device 140, for example, through the same transparent or portion, window or dome, or, optionally, through another transparent portion, window or dome, and may be received by optical system 150 and/or imager 146. In some embodiments, for example, optical system 150 and/or imager 146 may receive light, reflected from a body lumen, through the same window or dome through which illumination source(s) 142 illuminate the body lumen.

According to one embodiment, while device 140 traverses a patient's GI tract, the device 140 transmits image and possibly other data to components located outside the patient's body, which receive and process the data. Typically, receiving unit 112 is located outside the patient's body in one or more locations. The receiving unit 112 may typically include, or be operatively associated with, for example, one or more antennas, or an antenna array 124, for receiving and/or transmitting signals from/to device 140. Receiving unit 112 typically includes an image receiver storage unit. According to one embodiment, the image receiver 112 and image receiver storage unit are small and portable, and are typically worn on the patient's body (or located in close proximity to the patient's body) during recording of the images, at least until the image capturing procedure is determined to be terminated.

The receiving unit 112 may include, or be operatively associated with a signal detection unit 123, which may detect signals transmitted from, for example, device 140. The signal detection unit 123 may be coupled or included in the antenna or antenna array 124. The signal detection unit 123 may measure the power intensity, frequency, and/or rate of the received signal. The signal detection unit 123 may provide an indication, for example to the control/processing unit 122, regarding the type, strength, length, rate, content, and/or frequency of the received signal. Other parameters of the signal may be detected. For example, when an image signal is received from the device 140, the signal detection unit 123 may pass the signal strength and signal type to the control/processing unit 122. When the signal type changes to a beacon signal, or when no signal is being detected after a certain time-out period, the control/processing unit 122 may receive such notice, for example from the signal detection unit 123.

In some embodiments, it may not be possible to determine whether the device is in vivo or not. The receiving unit or control unit may also notify of such cases.

As will be explained in further detail below, the control/processing unit 122 may evaluate the current information available regarding the received device signal type, strength, length, rate, content, and/or frequency, and, based on the information, may determine whether the image capturing procedure is still in process, or has been completed or stopped. The control/processing unit 122 may output a notification regarding the termination of the image capturing procedure, for example through a notification unit 130, to a display which may be included in the receiving unit 112 or for example wirelessly to a remote or separate display unit. The notification may also indicate whether the termination is due to completion of the procedure, low battery power, external command, or due to other reasons, and whether it is permanent or temporary termination In some embodiments, device 140 may communicate with an external receiving and display system (e.g., workstation 117 or monitor 118) to provide display of data, control, or other functions. For example, power may be provided to device 140 using an internal battery, an internal power source, or a wireless system able to receive power. Other embodiments may have other configurations and capabilities. For example, components may be distributed over multiple sites or units, and control information or other information may be received from an external source.

Processor 114 may include a processing unit, processor or controller. The processing unit may include, for example, a CPU, a DSP, a microprocessor, a controller, a chip, a microchip, a controller, circuitry, an IC, an ASIC, or any other suitable multi-purpose or specific processor, controller, circuitry or circuit.

Data processor 114 may analyze the data received via external receiver/recorder 112 from device 140, and may be in communication with storage unit 119, e.g., transferring frame data to and from storage unit 119. Data processor 114 may provide the analyzed data to monitor 118, where a user (e.g., a physician) may view or otherwise use the data. In some embodiments, data processor 114 may be configured for real time processing and/or for post processing to be performed and/or viewed at a later time. In the case that control capability (e.g., delay, timing, etc) is external to device 140, a suitable external device (such as, for example, data processor 114 or external receiver/recorder 112 having a transmitter or transceiver) may transmit one or more control signals to device 140.

Monitor 118 may include, for example, one or more screens, monitors, or suitable display units. Monitor 118, for example, may display one or more images or a stream of images captured and/or transmitted by device 140, e.g., images of the GI tract or of other imaged body lumen or cavity. Additionally or alternatively, monitor 118 may display, for example, control data, location or position data (e.g., data describing or indicating the location or the relative location of device 140), orientation data, and various other suitable data. In some embodiments, for example, both an image and its position (e.g., relative to the body lumen being imaged) or location may be presented using monitor 118 and/or may be stored using storage unit 119. Other systems and methods of storing and/or displaying collected image data and/or other data may be used.

Typically, device 140 may transmit image information in discrete portions. Each portion may typically correspond to an image or a frame; other suitable transmission methods may be used. For example, in some embodiments, device 140 may capture and/or acquire an image once every half second, and may transmit the image data to the external receiving unit 112. Other constant and/or variable capture rates and/or transmission rates may be used.

Determining the cause of termination of the in vivo image capturing procedure may be complicated due to the variety of reasons that may cause the procedure to end. For example, the power supply of the in vivo imaging device may be depleted, causing the device to stop capturing images. According to some embodiments, the device may be programmed to stop taking images when a certain battery level threshold is reached. The remaining power may be used to transmit minimal power beacon signals from the device. The device may continue the low level beacon signal transmission for a predetermined period, for example for 48 hours or 7 days, or until the power source is completely depleted. According to some embodiments, the device may be preprogrammed to stop capturing images after a predetermined period has lapsed, for example 60 minutes or 10 hours of operation, or after a different fixed time period. The device may also be preprogrammed to stop the image capturing mode after detecting occurrence of a certain event in the capsule, or upon detection that the capsule reached a specific position, for example detection of entrance to the small bowel or another organ. In one example, the reception unit or signal detection unit external to the body may have a temporary or permanent failure, causing the receiving unit not to receive any images despite their transmittal by the imaging device. In another example, the capsule may have a hardware or software failure and may stop transmitting signals. In one embodiment, the receiving unit may analyze the received images in real time, for example a series of the last images which were properly received from the capsule, and determine whether the procedure is completed, for example when detecting images captured by the device that are not in vivo images. The device may receive a command to terminate the imaging procedure, for example from an external control unit.

Typically, in capsule endoscopy procedures, the patient and/or health care professional want to know when the imaging procedure has ended. The patient/doctor may also be concerned that the capsule has not been evacuated from the body, and notifying of the capsule evacuation relieves the patient's anxiety.

Accordingly, provided herein is a method for determining the end of an in vivo image capturing procedure and the evacuation of an autonomous in vivo device from the body.

Figure 2A:
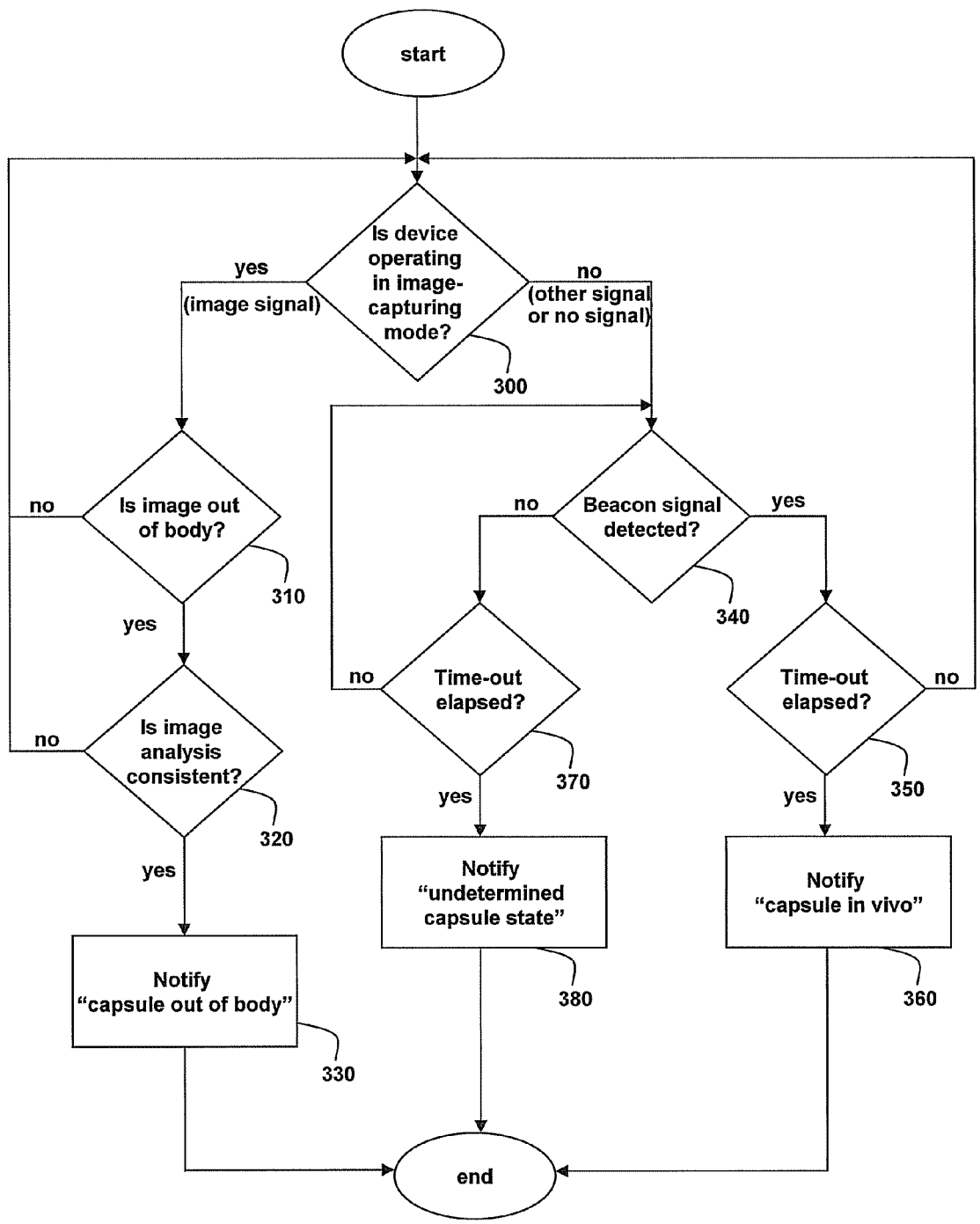
FIG. 2A is a flow chart of an exemplary method for determining if an in vivo imaging procedure has been terminated.

Reference is now made to FIG. 2A, which illustrates an exemplary method of determining termination of an image capturing procedure according to one embodiment of the present invention. According to one embodiment, the method may include the process of checking whether the in-vivo imaging device is in operating in image-capturing mode (step 300). Such a mode may be, for example, an image-capturing mode of the imager included in the device. The image-capturing operation mode may include transmission of image data from the device to an external receiving unit, and reception/storage of the image data by the receiving unit. The receiving unit may be, for example, the receiving unit 112 described above. The signal detection unit 123 may be used to determine whether the device is transmitting an image signal. In a next step of the method, the image may be analyzed, for example by a processing unit such as control/processing unit 122 (or by another unit, which may not necessarily be included in the receiving unit 112). The analysis may include determining whether the image is an in vivo image or an image taken out of the body of the patient (step 310).

The analysis, for example in real-time, whether an image is an in vivo image or an image captured out of the patient's body may be used for verifying if the received images are transmitted by the correct capsule. For example, if several patients are undergoing an image capturing procedure simultaneously, the receiving units may detect image signals transmitted from different imaging devices. This may require analyzing images, for example prior to swallowing the imaging device, and pairing or associating between a single transmitting device and a single receiving unit once the images are verified to be arriving from the correct imaging device. In one example, the verification may be performed during the initialization phase of the image capturing procedure, for example by pointing the capsule at a specific predetermined view or picture, and automatically detecting which capsule belongs to which receiving unit. In addition, some or all of the methods described here may include the step of generating a pairing or an association between the receiving unit and the appropriate capsule, for example in order to prevent errors or erroneous decisions which may take place if a receiving unit receives signals from a foreign capsule.

According to one embodiment, the image analysis may also include automatically determining whether the device has been swallowed or not, and it may allow notifying the patient or the health care specialist regarding the start of an in-vivo image capturing mode. In another embodiment, the image analysis may be used to detect in real-time whether the capsule has arrived at a certain in-vivo location, for example if the capsule has entered the stomach, the small bowel or the colon, and a notification may be provided based on such detection. The automatic detection that the imaging device has been swallowed (or that the device is in-vivo) may trigger the device to initiate, either automatically or by a command received from an external control unit, a specific mode of operation and/or to activate a specific component of the device such as a sensor, an illumination source, etc.

If the image is determined to be an in vivo image, the method may include returning to the step 300 of checking normal operation. However, if the image is determined to be an image taken outside of the patient's body, the method may include the step of checking whether the image analysis is consistent (step 320). For example, in one embodiment, a series of consecutive image may be analyzed, and only if a predetermined number of consecutive image are determined to be taken outside of the patient's body, then the image analysis is determined to be consistent and a notification may be made that the capsule is out of the body (step 330). The notification unit shown in FIG. 1 may provide such a notification, for example to the patient or to a health care specialist who is following the status of the patient's image-capturing procedure. If the image analysis is not determined to be consistent, for example 2 images were analyzed to be taken out of the body and then 2 images were analyzed as in-vivo images, then additional images may be checked, for example returning to steps 300/310 and analyzing the new images which may be transmitted from the imaging device.

In step 300, the device may be operating in another mode, which is not an image capturing mode. The device may not be operating at all, for example due to depleted battery or due to a component failure. In one embodiment, image signals with a high number of communication errors may be captured/received from the device, or no signal at all may be received. Such an occurrence may happen, for example, when the imaging device battery is almost depleted and the battery is operating in low voltage (a predetermined voltage level may be set). Such an occurrence may also happen when the imaging capsule is getting further away from the sensors, for example on its way out of the body. In a preferred embodiment, the battery will notify the receiving unit (or the receiving unit will check the battery registers status), and the receiving unit may transmit a command to the imaging device to switch to operation in beacon mode. The device may also switch automatically to beacon mode, for example as a result of other reasons such as the lapse of a time-out period that was preset for the procedure. In another occurrence, the receiving unit or the signal detection unit may not detect any signal from the imaging device. According to one embodiment, the signal detection unit or another component in the receiving unit may detect that the signal is a beacon-type signal (step 340). If a time out elapsed (step 350), for example a predetermined time period, a notification may be made that the capsule is in vivo (step 360). If a time-out has not elapsed, the operation mode may be rechecked (step 300).

If no signal is detected from the capsule (340), and a predetermined time-out elapsed (step 370), a notification may be made that the capsule state is unknown or undetermined (step 380). For example, it may not be possible to determine, for example based on the last images received from the device, if the device is still in the body or has been evacuated.

Figure 2B:
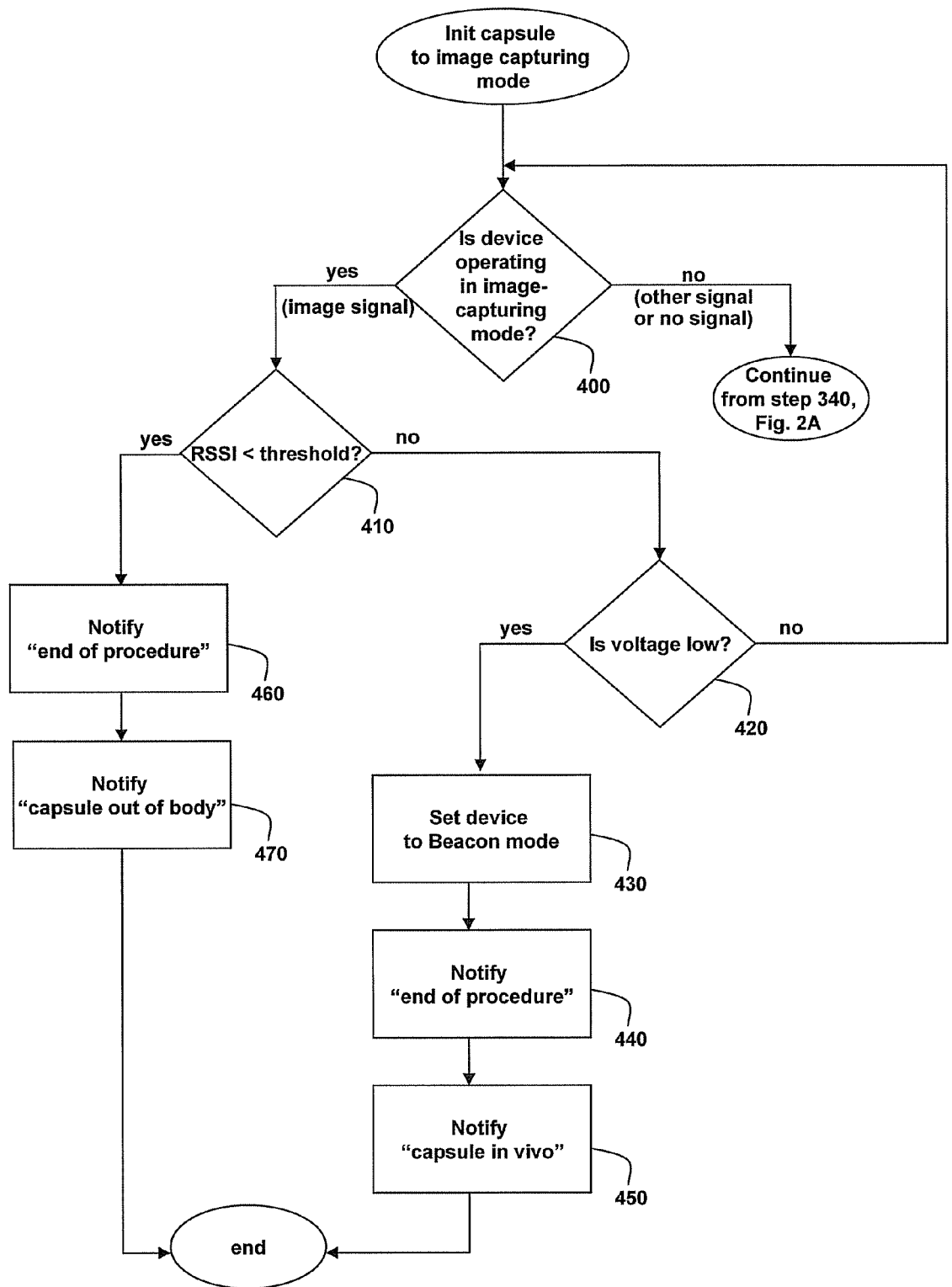
FIG. 2B is a flow chart of another exemplary method for determining if an in vivo imaging procedure has been terminated.

Reference is now made to FIG. 2B, which illustrates an additional example of a method of determining termination of an image capturing procedure. Similarly to the method illustrated in FIG. 2A, the current method may include the process of checking whether the in-vivo imaging device is in operating in image-capturing mode (step 400). If the mode is not determined as image capturing mode, i.e., another type of signal is detected or no signal is detected, the method may continue similarly to the embodiment described in FIG. 2A, step 340.

If the mode is determined as image capturing mode, for example image data is received by the external receiving unit, the RSSI (Received Signal Strength Indication, which provides the power level of the signal as received by the receiving unit) may be compared to an RSSI threshold level (step 410). The RSSI threshold level may be calculated in real-time, based on, for example, the average RSSI of the last 50 or 100 image signals, or the threshold may be preset to a specific value. Other methods of calculating the RSSI threshold may be used, such as a percentage of the highest RSSI which was recorded in the current procedure. If the RSSI is lower than the threshold, the next received signals may also be compared in order to verify that the reception level is consistent throughout a timeout period and not a temporary anomaly. If the RSSI is determined to be below the RSSI threshold level, the user may be notified that the procedure has ended and that the imaging device has exited the body (steps 460 and 470). If the RSSI is above the RSSI threshold level, the operation mode of the device may be rechecked (back to step 400).

If the RSSI comparison result has been determined to be above the threshold level, the imaging device's power (voltage) level may be checked (step 420). For example, the battery voltage level may be sampled, i.e. by a component of the imaging device, and the result may be transmitted to the receiving unit. The voltage level received from the capsule may be compared to a voltage threshold level, for example a predetermined value of 2.5 volt, or to a relative battery voltage level which may be, for example, 10% or 20% less than the initial (or highest) voltage level. The voltage level comparison may also be performed by a processing unit located internally in the imaging device. If the voltage is determined to be low, the device may be set to stop image capturing mode and switch to beacon mode (step 430). For example, the device may automatically switch to beacon mode based on the voltage level comparison result, or the device may receive a command from an external control unit, for example the receiving unit, to stop the image capturing mode and transit to another mode, such as beacon mode or telemetry mode. The device, or the external control unit, may then notify the user that the procedure has ended (step 440), and it may be determined that the device is still in vivo at this time (step 450). The determination may be automatic based on the change of modes, or may be verified by image analysis as explained above.

This method may be used instead or in addition to the method described in FIG. 2A. Other steps/methods may be used to determine termination of an image capturing procedure.

Figure 2C:
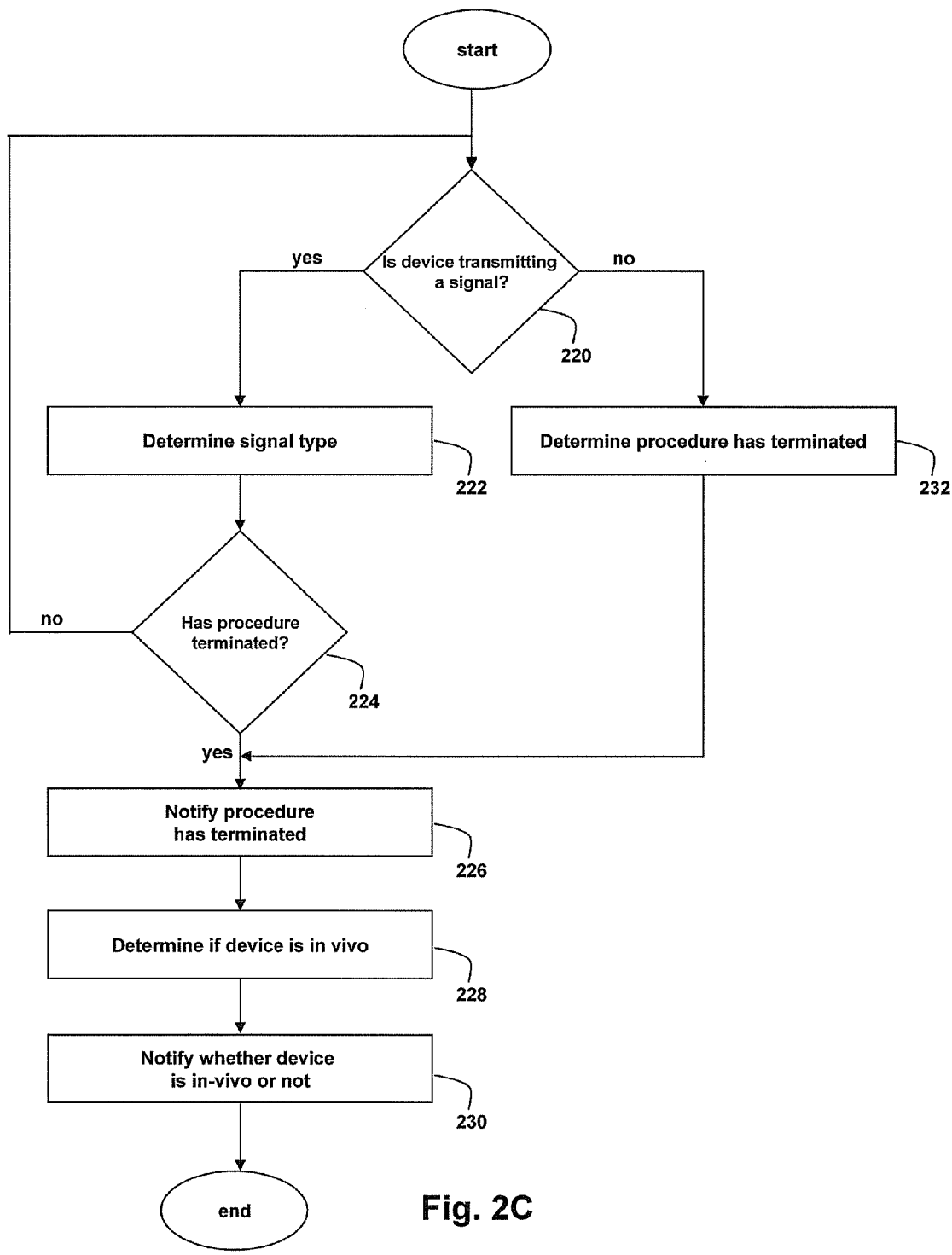
FIG. 2C is a flow chart of a general method for determining if an in vivo imaging procedure has been terminated.

Reference is now made to FIG. 2C, which illustrates a general method of determining termination of an image capturing procedure according to one embodiment of the present invention. In order to determine whether an in vivo imaging device, for example a capsule endoscope, has completed or stopped the image capturing procedure, it may initially be determined whether the device is transmitting any signal, as shown in step 220. The receiving unit 112 (shown in FIG. 1) may detect whether the device 140 is transmitting or not, for example based on a time-out period for receiving a signal from the device. The time-out period may be predetermined or preprogrammed with different parameters, such as different time-out periods, for different types of devices, for different frame rates or for different types of procedures. The time-out period may also occur upon detection of en event, such as detection that the imaging device reached a certain location in the patient's body. According to some embodiments, the receiving unit 112 may transmit a signal to the device and wait for a response from the device. In some cases, a temporary failure may prevent reception/detection of signals from the device by the signal detection unit 123, for example a cable may temporarily disconnect a reception antenna from the receiving unit. Therefore, according to some embodiments, the time-out period should be long enough to consider such occurrences. In some embodiments, such failures may be detected, and a notification may be made to allow the user to rectify the failure.

If the device is determined to be transmitting a signal, the signal type may be determined, as shown in step 222. The receiving unit 112 may determine the signal type, for example based on the signal length, the signal content, the signal strength, intensity, rate or the transmitted frequency. Other methods or parameters may be used to determine the signal type. Possible signal types may include, but are not limited to, image or video signals, telemetry signals and beacon signals of varying frequency, power, rate and/or content. According to one embodiment, if the received signal contains image data, the imaging procedure is determined to be still in process (step 224). If the received signal is determined to be a beacon signal, or another specific type of signal that is transmitted after the capsule stops capturing images, the imaging procedure may be determined to be terminated. Typically the control/processing unit 122 or other components in the receiving unit may determine termination of the image capturing procedure. Other components may be used to determine procedure termination. If the procedure is determined to be still in process, the method may include returning to step 220 of determining whether the device is transmitting any signal.

In some embodiments, the receiving unit 112 or a notification unit 130 which is operationally coupled to the receiving unit 112 may notify the patient of the termination of the procedure (step 226). The notification may be output on a portable display connected to the receiving unit (or to the notification unit), or may be announced by lighting or blinking a LED, by a vibrating mechanism or by a vocal signal provided with speakers which may be included in the receiving unit 112 or in the notification unit 130. Other methods of notifying are possible.

After determining the image capturing procedure is terminated, the control/processing unit may determine whether the imaging device 140 is still in the patient's body (step 228) or if it has been evacuated from the body. According to one embodiment, determining if the device is in vivo may be performed by analyzing the last images which were received from the in vivo device. Typically, the in vivo device is configured to capture images while the light sources are operating. However, in some embodiments, the in vivo device also captures images when the lights sources are not operating, and these images are used for example to remove noise from the images with light. Such images are called dark images. When the in vivo imaging device is in vivo, the dark images are usually substantially black. When the device is out of the patient's body, the dark images are typically captured with external light, which causes them to be substantially lighter than those taken in vivo. Analyzing the light intensity in the dark images sent from the device may enable determining whether the images were taken in vivo or externally, and therefore may allow to notify the patient whether the device is in vivo or not (step 230), based on whether the last image (or set of images) which were received from the device were determined to be in vivo images or not. Other methods of image analysis may be used, for example analyzing the last received images to identify colors that are typical to images captured in vivo, versus images that have other colors which may indicate that the capsule has left the body. Another possible embodiment is to present the last images, for example the 20 last images which were received with no errors or with a low error/noise level, onto an LCD screen or other portable display which may be included in the receiving unit 112, and the user (doctor or health care specialist for example) may decide whether the last images were captured in vivo or out of the body. Such a process may prevent the need to download the images and compile them for viewing for determining whether the device has been evacuated from the body or not.

Determining whether the device is still in the patient's body may be performed using other methods. For example, the receiving unit 112 may be notified of a low battery status in the capsule 140. If the receiving unit 112 receives no notification of a low battery status, however suddenly stops receiving signals from the imaging device, it may be determined that the capsule was excreted from the body. In cases of low battery status notification, the frame rate may be changed, for example dropped to 10% of previous rate, or to a rate of 1 frame per minute or another predetermined rate. The images captured in this low frame rate mode may be provided to the user, for example on a portable screen or on an LCD display which may be included in the receiving unit 112. The user (for example the patient) may be notified of the low battery status, and a doctor may check the displayed images. This embodiment may enable to determine whether the imagining device has left the body, for example in cases that the battery power may run out earlier than expected/wanted, or in cases that the capsule movement was slower than expected. In cases that there has been a notification of low battery power, then the receiving unit stopped receiving signals, it may be determined that the device is still in the patient's body at the end of the procedure. Preferably, the device may be switched to a beacon mode in such cases.

Other methods of determining whether the device is in vivo or not may be used. For example, a pressure measurement unit may be coupled to device 140, and the changes of in vivo pressure which may be typically higher than external pressure, may be detected by such unit. A significant drop in pressure measurement may indicate the moment of the capsule exiting the body. In another embodiment, an accelerometer which may be included in device 140 may measure the acceleration of the device, and determine that the capsule has been evacuated from the body when a certain acceleration threshold is reached, for example when a capsule is detected to be free-falling. In yet another embodiment, the in vivo device may comprise an RF identification tag or chip, for example a passive RFID tag which may be very small and requires no power source, may be inserted into a capsule. When the time period of the procedure is over, the health care professional may check if the device is still in the patient's body by scanning the patient's body with an appropriate RF scanner.

If the device is not transmitting any signals, for example in the case no signals are detected by the signal detection unit 123, the termination of the image capturing procedure may be determined (step 232). According to some embodiments, a notification of procedure termination may be provided to the user (step 226). Some or all of the other steps may optionally be performed.

The processes presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems appears from the description herein. In addition, embodiments of the present invention are not described with reference to any particular programming language. It will be appreciated that a variety of programming languages may be used to implement the teachings of the invention as described herein.

Unless specifically stated otherwise, as apparent from the discussions herein, it is appreciated that throughout the specification discussions utilizing terms such as "estimating", "processing", "computing", "calculating", "determining", or the like, typically refer to the action and/or processes of a computer or computing system, or similar electronic computing device (e.g., a "computer on a chip" or ASIC), that manipulate and/or transform data represented as physical, such as electronic, quantities within the computing system's registers and/or memories into other data similarly represented as physical quantities within the computing system's memories, registers or other such information storage, transmission or display devices.

It will be appreciated by persons skilled in the art that the present invention is not limited to what has been particularly shown and described hereinabove.

Having described preferred embodiments of the invention with reference to the accompanying drawings, it is to be understood that the invention is not limited to the precise embodiments shown and described hereinabove. Rather, various changes and modifications may be effected therein by those skilled in the art without departing from the scope or spirit of the invention, and the scope of the present invention is defined only by the claims, which follow.

What is claimed is:

1. A method of determining termination of an in vivo capturing procedure by an autonomous device comprising the steps of:
   determining whether a condition with respect to said device has been met;
   if said condition has been met, setting the device to a beacon mode;
   receiving a signal from the device;
   determining if said signal is a beacon signal, an imaging signal or neither;
   if the signal is a beacon signal, determining that the in vivo image capturing procedure is terminated; determining, based on analysis of images captured by the autonomous device, whether the autonomous device is in vivo; and
   providing a notification of whether or not the autonomous device is in vivo.

2. The method of claim 1, further comprising, if the in vivo image capturing procedure is terminated, providing a notification.

3. The method of claim 1, further comprising detecting the signal type based on said signal's power intensity, frequency, rate, length or content.

4. The method of claim 1, further comprising the step:
   if no signal is received from the device, determining termination of the image capturing procedure.

5. The method of claim 1, further comprising using an RF scanner to determine if the device is still in the patient's body.

6. The method of claim 1, further comprising based on said signal type, determining if the in vivo image capturing procedure is initiated.

7. The method of claim 1, wherein the condition is a low battery voltage; a completed, stopped or terminated image capturing procedure; a lapse of a predetermined period of time; or the capsule having reached a predetermined position in vivo.

8. The method of claim 1, wherein the step of determining that the in vivo image capturing procedure is terminated is done only if a predetermined period has elapsed.

9. A system for determining termination of an in vivo image capturing procedure comprising:

an autonomous imaging device for imaging a body lumen, the device comprising a sensor for sensing a condition in vivo and a transceiver to transmit signals wirelessly, the transceiver being operable at least in an image capturing mode or in a beacon mode;

a control unit to switch between the image capturing mode and the beacon mode based on the condition sensed;

a receiving unit to detect a signal transmitted from the imaging device and to determine if the detected signal is an image signal, a beacon signal or neither;

a processing unit to determine whether an image capturing procedure has terminated, based on analysis of the detected signal, the processing unit further to determine if the autonomous imaging device is in vivo by analyzing images received from the autonomous imaging device and to provide a notification of whether or not the autonomous imaging device is in vivo.

10. The system of claim 9 wherein the receiving unit detects the received signal power intensity, frequency, rate, length or content.

11. The system of claim 9 further comprising a notification unit to notify a user if image capturing procedure has or has not terminated.

12. The system of claim 9 wherein the processing unit to determine if the autonomous imaging device is in vivo is provided in the receiving unit.

13. The system of claim 9 wherein the analyzed images are the last image or plurality of images that were received from the imaging device.

14. The system of claim 9 wherein the autonomous imaging device further comprises an RF identification unit.

15. The system of claim 9, wherein the condition is a low battery voltage; a completed, stopped or terminated image capturing procedure; a lapse of a predetermined period of time; or the capsule having reached a predetermined position in vivo.

* * * * *